US010350853B2

(12) United States Patent
Thomas

(10) Patent No.: US 10,350,853 B2
(45) Date of Patent: Jul. 16, 2019

(54) FORMED FILM WITH MICRO-CELLS AND MACRO-DEPRESSIONS

(71) Applicant: Tredegar Film Products Corporation, Richmond, VA (US)

(72) Inventor: Paul Eugene Thomas, Terre Haute, IN (US)

(73) Assignee: TREDEGAR FILM PRODUCTS CORPORATION, Richmond, VA (US)

( * ) Notice: Subject to any disclaimer, the term of this patent is extended or adjusted under 35 U.S.C. 154(b) by 357 days.

(21) Appl. No.: 14/668,258

(22) Filed: Mar. 25, 2015

(65) Prior Publication Data

US 2015/0273793 A1    Oct. 1, 2015

Related U.S. Application Data

(60) Provisional application No. 61/970,297, filed on Mar. 25, 2014.

(51) Int. Cl.
*B32B 3/30* (2006.01)
*C08J 5/18* (2006.01)
(Continued)

(52) U.S. Cl.
CPC .......... *B32B 3/30* (2013.01); *A61F 13/15731* (2013.01); *A61F 13/5122* (2013.01);
(Continued)

(58) Field of Classification Search
CPC ........ Y10T 428/24661; A61F 13/51104; A61F 13/51394; A61F 13/15731; A61F 13/5122; B32B 3/30
See application file for complete search history.

(56) References Cited

U.S. PATENT DOCUMENTS 2,836,863 A * 6/1958 Denker .................... B27D 1/06
156/91
4,327,730 A * 5/1982 Sorensen .............. A61F 13/512
428/131
(Continued)

FOREIGN PATENT DOCUMENTS

CN        1078134 A    11/1993
CN        1105844 A     8/1995
(Continued)

OTHER PUBLICATIONS

International Search Report dated Jun. 1, 2015, for International Patent Application No. PCT/US2015/022532.
(Continued)

*Primary Examiner* — Donald J Loney
(74) *Attorney, Agent, or Firm* — Karceski IP Law, PLLC

(57) ABSTRACT

A formed film with micro-cells and macro-cells or depressions may be disclosed. For example, the film may include a lands. Each of the lands may include micro-cells thereon. The micro-cells may have a first orientation. The film may further include macro-depressions adjacent to at least one respective land. Each of the macro depressions may include additional second micro-cells. Those additional micro-cells may have a second orientation. The second orientation includes an orientation that is an inverse of the first orientation (e.g., is in an opposite direction of the first orientation).

11 Claims, 12 Drawing Sheets

(51) Int. Cl.
  *B32B 27/32* (2006.01)
  *A61F 13/511* (2006.01)
  *A61F 13/513* (2006.01)
  *A61F 13/15* (2006.01)
  *B26F 1/38* (2006.01)
  *A61F 13/512* (2006.01)
  *B29C 59/04* (2006.01)
  *B29C 59/02* (2006.01)

(52) U.S. Cl.
  CPC .. *A61F 13/51104* (2013.01); *A61F 13/51394* (2013.01); *B26F 1/384* (2013.01); *B32B 27/32* (2013.01); *C08J 5/18* (2013.01); *B29C 59/04* (2013.01); *B29C 2059/023* (2013.01); *C08J 2323/06* (2013.01); *Y10T 428/24661* (2015.01)

(56) References Cited

U.S. PATENT DOCUMENTS

| | | | |
|---|---|---|---|
| 4,614,679 A * | 9/1986 | Farrington, Jr. | A47L 23/266 15/215 |
| 4,629,643 A * | 12/1986 | Curro | A61F 13/5146 428/131 |
| 4,690,679 A | 9/1987 | Mattingly, III et al. | |
| 4,772,444 A | 9/1988 | Curro et al. | |
| 4,859,519 A | 8/1989 | Cabe, Jr. et al. | |
| 6,599,612 B1 | 7/2003 | Gray | |
| 6,849,319 B2 | 2/2005 | Cree et al. | |
| 7,204,907 B2 | 4/2007 | Cree et al. | |
| 7,601,415 B2 | 10/2009 | Cree et al. | |
| 8,168,102 B2 | 5/2012 | Di Berardino | |
| 8,585,951 B2 | 11/2013 | Muhs et al. | |
| 8,858,591 B2 | 10/2014 | Preinitz et al. | |
| 2009/0221979 A1 * | 9/2009 | Huang | A61F 13/51108 604/367 |
| 2011/0119850 A1 * | 5/2011 | Mallory | A47L 13/16 15/209.1 |

FOREIGN PATENT DOCUMENTS

| | | |
|---|---|---|
| EP | 0203823 A2 | 12/1986 |
| EP | 1923028 A1 | 5/2008 |
| JP | S569401 A | 1/1981 |
| JP | H01264839 A | 10/1989 |
| JP | 2006511367 A | 4/2006 |
| JP | 62057975 A | 3/2015 |
| WO | WO 9301047 | 1/1993 |
| WO | WO 2004058121 A1 | 7/2004 |
| WO | 2013091150 A1 | 6/2013 |

OTHER PUBLICATIONS

International Preliminary Report on Patentability dated Sep. 27, 2016, for International Patent Application No. PCT/US2015/022532.
European Office Action dated Jan. 18, 2019, for European Patent Application No. 15714383.5.
Chinese Office Action dated Jan. 22, 2019, for Chinese Patent Application No. 201580027261.5.
Japanese Office Action dated Jan. 24, 2019, for Japanese Patent Application No. 2016-558708.

* cited by examiner

Prior Art

Prior Art

Prior Art

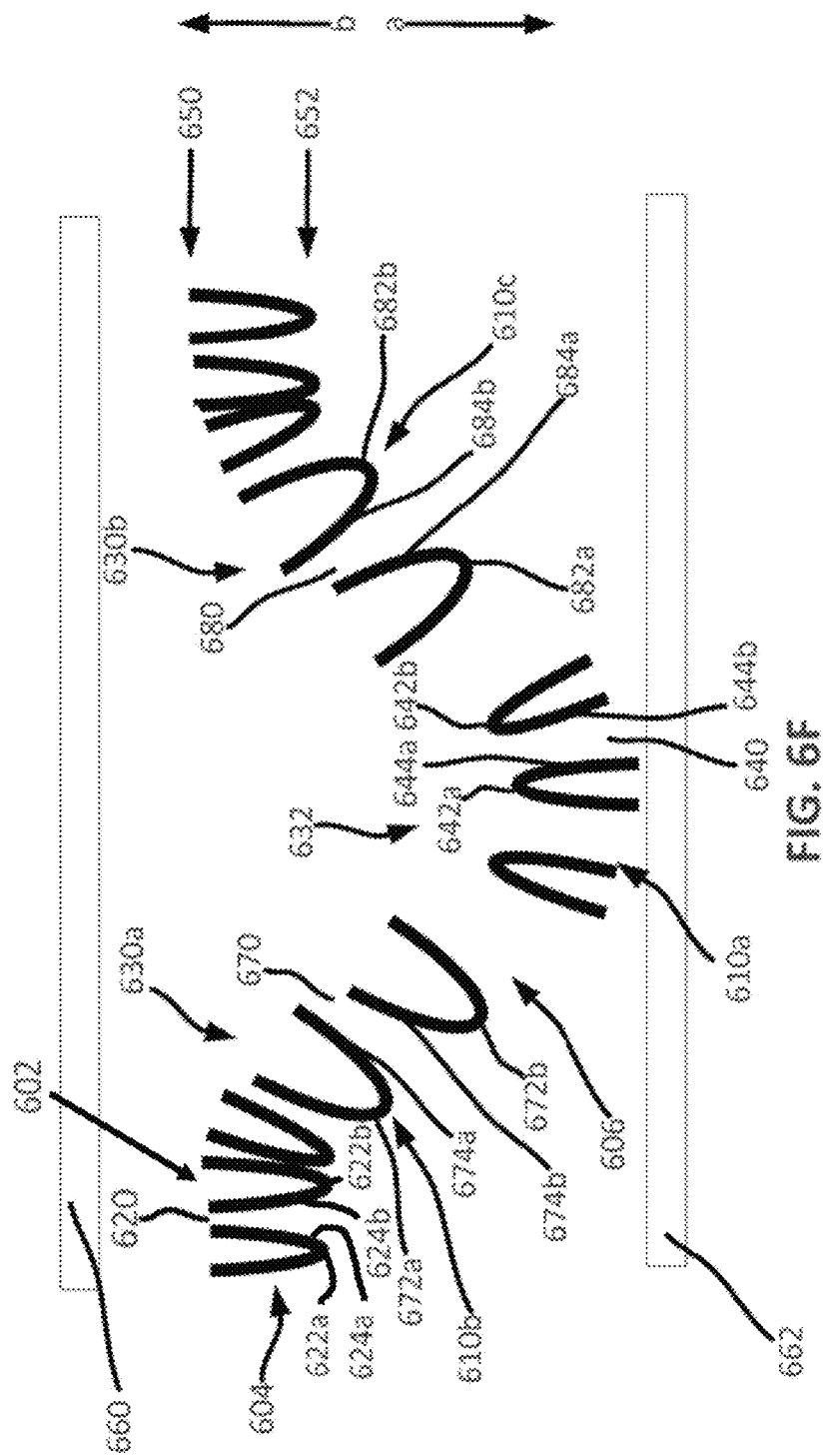

FORMED FILM WITH MICRO-CELLS AND MACRO-DEPRESSIONS

CROSS-REFERENCE TO RELATED APPLICATIONS

This application claims the benefit of the U.S. Provisional Application No. 61/970,297, filed Mar. 25, 2014, which is hereby incorporated by reference herein.

BACKGROUND

An absorbent device is typically comprised of a topsheet, a fluid acquisition distribution layer, an absorbent core and a backsheet. The topsheet contacts the skin of the user of the device and transmits the fluid exudate toward the absorbent core which captures and stores it. The backsheet is the outermost layer and provides a liquid barrier against staining or soiling the clothing by preventing leakage or the passing of liquids stored in the core. Both the backsheet and the topsheet can be comprised of a thin layer of polymer film. "Thin" is historically in a general range of less than 50 microns but greater than 10 microns.

Since the advent of disposable diapers where a quiet material, absent from crinkling noise, was desired, it has been desired to impart a three dimensional aspect to a thin polymeric film used in absorptive devices. Such patterns of three dimensional aspects may be formed on lands of the film and may include macro-cells that may include larger three-dimensional aspects and micro-cells that may include smaller three-dimensional aspects. Such aspects typically provide the film layers with one or more following attributes: flexural softness and/or quietness due the 'pleating' aspect which lowers the resistance to the mechanical stress used to crumple or bend the film; lower gloss, or lack of sheen, by diffusing the reflected light; softness or silkiness to the touch, by creating a desired 'tactile' impression to the fingertips derived by pattern type and spacing and array, and specifically for tactile softness; a thinning which enables or allows a flexural bending as touch may be applied; an aesthetic appeal with patterns of flowers or ribbons or other designs found to be pleasing to a particular market segment of consumers; and the like. Additionally, one or more openings or apertures may be formed through the topsheet that may allow liquid to pass. In examples, the openings or apertures may be formed by the three-dimensional aspects such as the micro-cells and/or macro-cells, for example, at an end or base thereof.

Unfortunately, current three-dimensional aspects that may include micro-cells and/or macro-cells or depressions do not include an array or field of micro-cells in a macro-cell that may point in different directions (e.g., some of the micro-cells may be inverted from other micro-cells).

SUMMARY

A formed film with micro-cells and macro-cells or depressions may be disclosed. The film may be used in an article such as a diaper. When used, some of the micro-cells may be oriented toward skin of a user of the article (e.g., a first orientation) and other micro-cells may be orientated toward a core of the article (e.g., a second orientation). For example, the film may include a land. The land may include a first micro-cell thereon. The first micro-cell may have a first orientation (e.g., toward the skin). The film may further include a macro-depression adjacent to the land. The macro depression may include a second micro-cell. The micro-cell may include a second orientation (e.g., toward the core). The second orientation includes an orientation that is an inverse of the first orientation (e.g., is in an opposite direction of the first orientation).

In an embodiment, the film may include a top surface and a bottom surface. Each of the first plurality of micro-cells may include a tip at the top surface of the film, a first and second valley at the bottom surface of the film, and a first and second sidewall extending (e.g., in a first z-direction toward a core when used in an article) from the tip at the top surface of the film to the respective first and second valleys at the bottom surface of the film. Such an embodiment with the tip at the top surface of the film, the first and valleys at the bottom surface of the film, and the first and second sidewalls extending therebetween may be the first orientation (e.g., an orientation toward the skin).

Further, according to an embodiment, each of the second plurality of micro-cells may include a tip at the bottom surface of the film, a first and second valley at the top surface of the film, and a first and second sidewall extending (e.g., in a second z-direction that is opposite of the first z-direction) from the tip at the bottom surface of the film to the respective first and second valleys at the top surface of the film. Such an embodiment with the tip at the bottom surface of the film, the first and valleys at the top surface of the film, and the first and second sidewalls extending therebetween may be the second orientation (e.g., an orientation toward the core).

The Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to any limitations that solve any or all disadvantages noted in any part of this disclosure.

BRIEF DESCRIPTION OF THE DRAWINGS

A more detailed understanding of the embodiments disclosed herein may be had from the following description, given by way of example in conjunction with the accompanying drawings.

FIG. 6F depicts an example of the film of FIG. 6E along the lines E-E.

DETAILED DESCRIPTION

A detailed description of illustrative embodiments will now be described with reference to the various Figures. Although this description provides a detailed example of possible implementations, it should be noted that the details are intended to be exemplary and in no way limit the scope of the application.

A formed film, methods, and/or processes are disclosed for providing a field or array of micro-cells on lands and macro-depressions of the film. In an example, at least a portion of the micro-cells in the field or array of micro-cells on the lands may be inverted from the macro-cell and/or other micro-cells in the field or array of micro-cells. For example, micro-cells on the lands of the formed film may be oriented in a first orientation (e.g., an orientation toward the skin when the film may be used as a topsheet in an article such as diaper). Additionally, micro-cells that may extend into the macro-depressions may be oriented in a second orientation that is opposite of the first orientation (e.g., an orientation toward a core of the article).

Figure 1A:
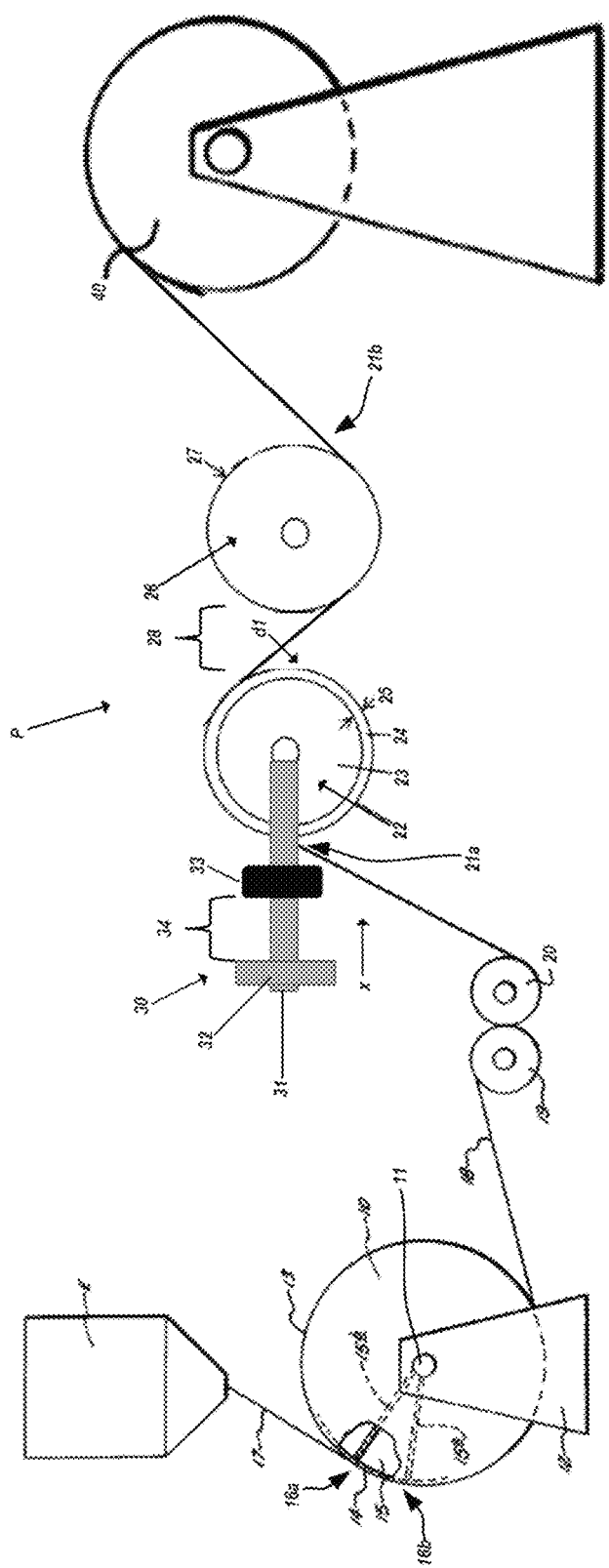
FIG. 1A depicts an example embodiment of a process or method for forming a film with some micro-cells pointing toward skin when used in an article and other micro-cells pointing to a core of the article not engaged.
Figure 1B:
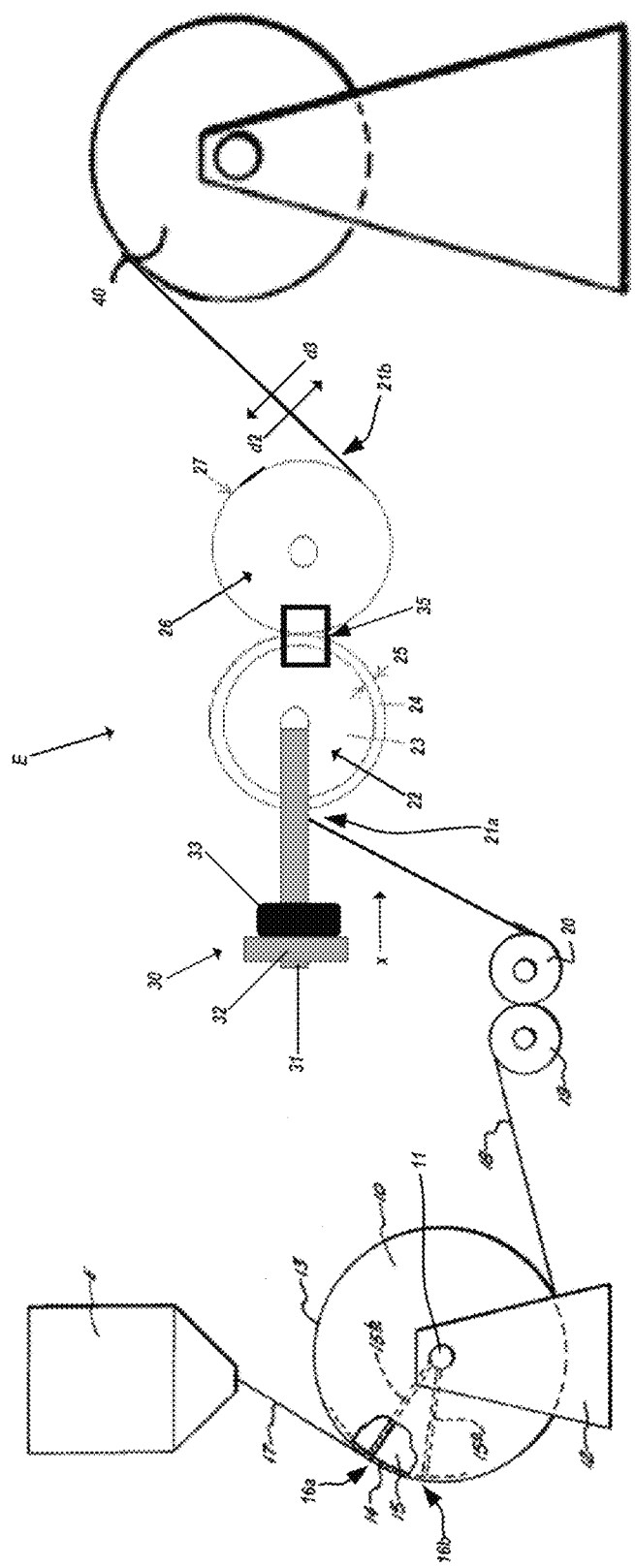
FIG. 1B depicts an example embodiment the process or method of FIG. 1A engaged.
Figure 1C:
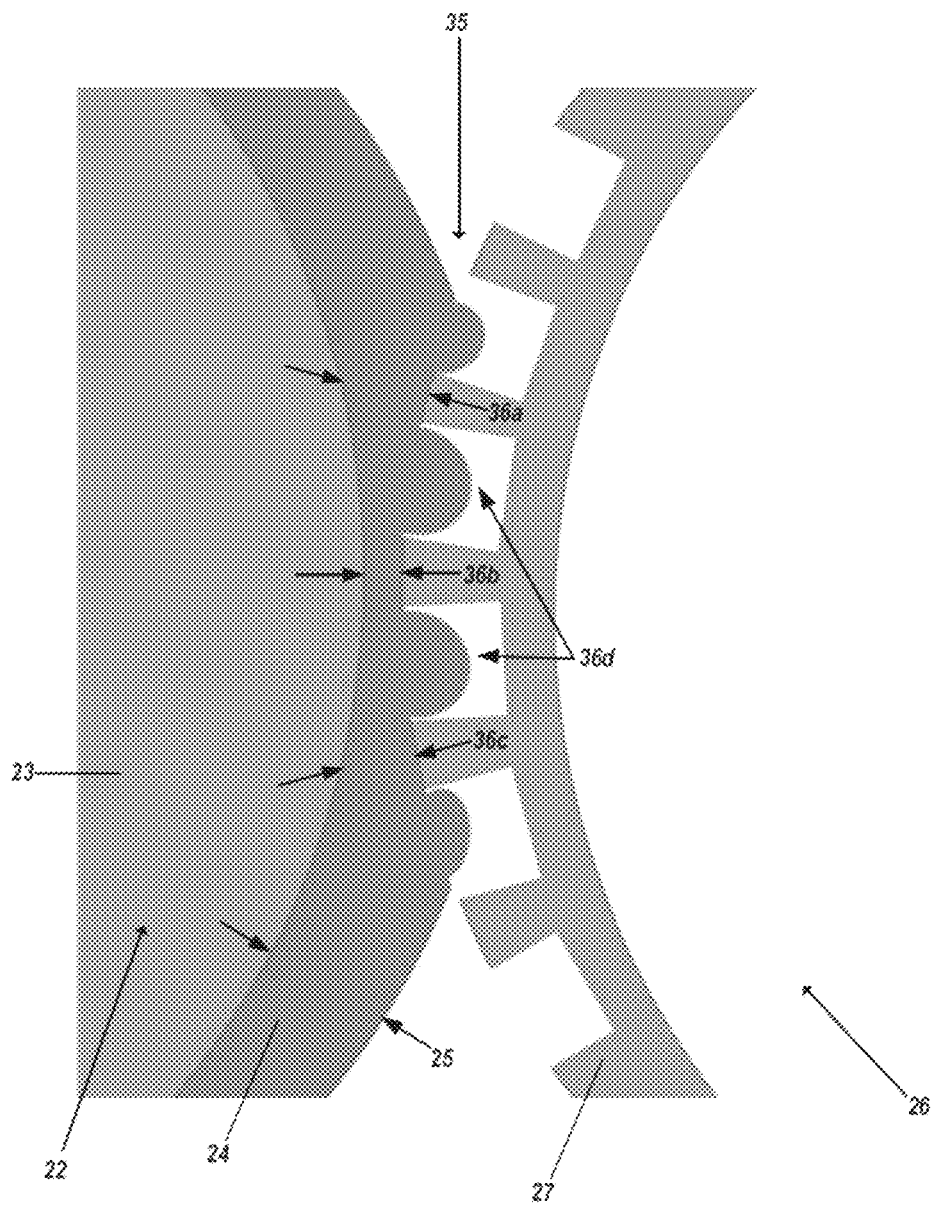
FIG. 1C depicts an exploded view of a portion of the process or method of FIG. 1B engaged.

FIGS. 1A-1C depicts an example process or method for forming a film with micro-cells in a macro-cell or depression where at least a portion of the micro-cells may be inverted from, for example, the macro-cells or depressions and/or other micro-cells on lands of the film. As shown, an apparatus for carrying out the process or method to form a sheet with a field of micro-cells may include a rotary cylindrical drum 10 that may be supported at each end by a centrally disposed axle 11 and a stationary axle supports 12. The drum 10 may have a cylindrical surface 13. In an example, the cylindrical surface of the drum roll 10 may be perforated such that air may pass through it. The drum 10 typically comprises on its outer surface a patterned forming screen 14. The screen 14 may be mounted around the surface 13 of drum 10 and may rotate with the drum 10. The screen 14 may be a welded or non-welded cylinder screen. Forming screens for imparting a formed film with a pattern of micro-cells are well known in the art. They may include a variety of nickel plated screens or machined metal screen, such as punched screens. Photo etched plates aligned and laminated in a stack may be used in an example. The patterned forming screens may also include laser engraved screens comprised of thermoplastic polymers or thermoset rubbers.

The screen 14 may be formed as an integral unit adapted to be slipped on the drum 10 from an end thereof and then secured thereto in any of the suitable manners known in the art. Additionally, the drum 10 and/or the screen 14 may rotate. To rotate the screen 14 and/or the drum 10, a gear drive (not shown) may be provided and used. The gear drive may be configured or adapted to mesh with one or more gears (not shown) that may be provided on the drum 10 itself and/or a pulley drive (not shown) may be connected to the drum 10 by one or more caps (not shown) provided on the ends thereof. According to an example, gear drives or gear belt pulleys may be recommended for use as they will not slip; whereas, a V-belt pulley or smooth belt system might slip under a load.

A vacuum chamber 15 may also be provided. The vacuum chamber 15 may be used to create a pressure differential between the respective surfaces of a molten web or thermoplastic sheet to cause the sheet to flow into the perforations provided in the screen 14 and, thus, perforate the sheet. In an example, the vacuum chamber 15 may be positioned within the drum 10, for example, along the axis thereof. As shown, the vacuum chamber 15 may open over a portion of the periphery of the surface 13 of the drum 10.

As shown in FIGS. 1A-1B, plates 15a, 15b may define the vacuum chamber 15. In an example, to provide an effective seal of a leading and trailing edges 16a, 16b, respectively, of the vacuum chamber 15, seals (not shown) may be provided in the plates 15a, 15b to form a seal against the surface 13. The seals may be made of rubber or other suitable material. Further, according to an embodiment, the plates 15a and 15b may be stationary and rigidly affixed to axle 11 or other suitable means, such as a manifold pipe, such that the vacuum chamber 15 may remain in a fixed or stationary position in the drum 10. As such, the vacuum, chamber 15 may be sealed at each of the points except, for example, the peripheral openings on the drum 10 and may be evacuated or reduced in pressure by pumping equipment connected to the vacuum chamber 15 in any suitable manner.

In the example of FIGS. 1A-1B, located above and adjacent to the drum 10 may be extruder E. The extruder E may be used to extrude a molten web or thermoplastic sheet 17 onto the drum 10. As the web or sheet 17 travels downwardly from extruder E, the web or sheet 17 may contact the screen 14 which may be turning counter-clockwise with the drum 10. The screen 14 may carry the web or sheet 17 over the vacuum slot 15 that may cause the thermoplastic material to be drawn into the openings in screen 14 and thereby perforated to form a perforated film with a field or array of micro-cells that may point in a common direction. The film 18 may continue to travel around the drum 10 and is removed from the screen 14 and conveyed between rolls 19 and 20.

From the roll 20, the perforated film 18 is conveyed between roller 22 and roller 26. The roller 22 may include a core 23 and an outer layer 24. The core 23 may be a solid core typically made of a robust steel to avoid deflection. The outer layer 24 is a material of a different hardness than the core 23, the hardness being less than the hardness of the core 23 and having the ability to be elastically compressed (returns to an original length when compressive forces are removed). A suitable embodiment of the outer layer 24 may be a closed-cell or open-cell foam rubber layer. The outer layer 24 may have a non-compressed original thickness 25. In example embodiments, the foam has a thickness from about 0.15 inches to 0.75 inches, and ideally will range from 0.25 inches to 0.50 inches. The perforated film 18 is conveyed between roller 22 and roller 26 by contacting the outer layer 24 of roller 22 and subsequently contacting the roller 26.

The roller 26 may be solid and made of, for example, steel or non-ferrous metals such that the roller may avoid as much deflection as possible. The roller 26 may further include an outer surface 27. The outer surface 27 may include a pattern of depressions. The pattern of depression may be machined into the outer of surface of a metal roller. Further, the outer surface 27 may be constructed from a patterned cylinder that may be placed over the metal roller to provide the pattern of depressions. The outer cylinder may formed by machining a metal cylinder or laser engraving thermoplastic polymer cylinders or thermoset rubber cylinders. The outer layer 27 may be wrapped or slip-fit over the base metal roller 26. The pattern of depressions may include any shape, size, and/or the like desired for the macro-cells of a formed film topsheet or an acquisition distribution layer, which are well known in the art. In examples, the cells and pattern of depressions that form the cells may be hexagonal, circular, oval, elliptical, and/or polygonal.

As shown in FIG. 1A, the rollers 22 and 26 may be in a pre-engaged position P. In the pre-engaged position P, the roller 22 and the roller 26 may include a gap 28 therebetween that is adjustable. The gap 28 may be adjusted by an engagement mechanism 30. The engagement mechanism 30 may include an actuator shaft 31, a first stop 32, and a second stop 33. The first stop 32 may be affixed to and may move with the actuator shaft 31. Further, the second stop 33 may be present to or anchored to a fixed position independent of the actuator shaft 31 and first stop 32 such that the actuator shaft 31 may reciprocally travel through the second stop 33. The first stop 32 may come into contact with the second stop 33 as described herein during the reciprocating travel of the actuator shaft 31.

In the pre-engaged position 30 shown in FIG. 1A, the gap 28 between the roller 22 and the roller 26 may be provided, for example, from the actuator shaft 31 and first stop 32 being retracted away from the second stop 33. Such a refraction as shown may create a retraction gap 34 between the first and second stops 32, 33. The retraction gap 34 may correspond to and may control the gap 28 between the roller 22 and the roller 26. As shown, in an example, the film 18 may be laced onto the outer layer 24 of the first roller 22 at entry point 21a when the engagement mechanism 30 may be in the pre-engaged position P. When contacting the outer layer 24 of the first roller 22, the film 18 may include a pattern of micro-cells that have a multiplicity of three dimensional protrusions with a common Z-direction orientation in one direction such as direction d1.

As shown in FIG. 1B, the engagement mechanism 30 may be in an engaged position E. In the engaged position E, the roller 22 may be actuated to a distance of 5%-15% of the outer layer 24 original thickness 25 with the ideal gap of the process embodiment being 10%. For example, the actuator shaft 31 may travel in a direction x until first stop 32 may be stopped from further motion by contacting the second stop 33, which the actuator shaft 31 travels through. Such an actuation until the first stop 32 is against second stop 33 may create a collapse point 35. The collapse point 35 may correspond to and may be controlled by setting the second stop 33 to a pre-set position. The pre-set position may result or cause the outer layer 24 to be collapsed 5%-15% (e.g., as shown at 36a-36c, for example, in FIG. 1C) of the distance of original outer thickness 25 at the collapse point 35.

FIG. 1C illustrates an example magnified view of the collapse point 34. As shown, the collapse point 35 may be between the solid core 23 and outer surface 27 of the second roller 26 such that the film 18 may be passed between the first roller 22 and the second roller 22. Collapsed foam rubber 24 may then expands into the open cavities of the depression (e.g., as shown in 36d, for example) of the forming roller 27 to form macro-cells and/or invert micro-cells as described herein.

As described herein and shown in FIGS. 1A-1B, the film 18 entering at the point 21a may include of a pattern of micro-cells that have a multiplicity of three dimensional protrusions with a common z-direction orientation in one direction, for example, direction d1 with respect to the film 18. In an example, the pattern of micro-cells may be formed by vacuum forming, for example, using the drum 10 as described herein. Further, the pattern of micro-cells may be formed by hydroforming, embossing, needle punching or any other suitable method that may puncture apertures (three dimensional protrusions) with a common z-direction orientation in one direction such as micro-cells in the film 18.

As shown in FIGS. 1B-1C, as the film 18 passes through the point 35 when the rollers 22 and 26 may be the engaged position E, a pattern of macro-cells may be formed in the field of micro-cells with a common z-direction depth that is oriented in a common direction. The macro-cells may be larger than the micro-cells, may be fewer in quantity than the micro-cells on the film, and may be spaced apart from other macro-cells such that there may be a pattern of land area between the macro-cells. The macro-cells formed may include a portion of micro-cells within. Such micro-cells may extend and be alternated in direction from the direction d1 of other micro-cells. For example, the space between the macro-cells may be referred to as lands in formed film structures and is understood in the art to describe the film encompassing apertures in a film structure. After forming the macro-cells with the engagement mechanism in the engaged position, such lands may include substantially unaltered micro-cells, for example, in direction d1. A portion of the micro-cells that may be included in the macro-cells may be altered from the micro-cells on the lands (e.g., may not follow direction d1 or may be inverted from direction d1) as described herein.

After forming the macro-cells, the film 18 may pass long the roller 26 to exit point 21b. As shown, upon leaving the roller at exit point 21b, the macro-cells may extend in a direction d2 and at least some of the micro-cells such as the micro-cells remaining in the land areas between the macro-cells may point in direction d3 which is the opposite direction of the orientation of the direction d2 of micro-cells that may remain on the lands of the film 18. Further, at least a portion of micro-cells that may be included in and/or along the macro-cells or depression may also point in direction d3. As such, when the film 18 may exit at point 21b, the film 18 may have at least some micro-cells oriented in the direction d2 and macro-cells or macro-depressions and some of the micro-cells in the macro-cells or macro-depressions oriented in the direction d3. After exiting at 21a, the film 18 may continue onto a wind up roll 40 (e.g., directly from the roller 26 or via one or more tension rolls between (not shown) between the roller 26 and the wind up roll 40).

The micro and macro cells produced by the methods or process described herein may be constructed of various selected mesh counts; i.e., a selected cell pattern with a selected cell diameter and width of the lands or spaces between the apertures. The "mesh count" may be the number of cells aligned in one inch of distance. As such, what may be represented as a micro-cell herein may generally be comprised of mesh counts greater than 35 and a macro-cell (or depression area) herein may generally be comprised of mesh counts less than 35. In the examples herein, a 60 mesh film was used for the pattern of micro-cells. In such examples, the aperture of the micro-cells tapers and thins toward its open tip, and the open tip diameter is from about 0.005 to 0.008 inches with a land width of about 0.002 to about 0.004 inches.

Further, in such examples, the macro-cells were about an 8.7 mesh with an elongated hexagonal pattern in their aligned direction. The long axis (e.g., typically aligned in the Machine Direction) is about 0.075 inches and the shorter axis (e.g., typically aligned in the Cross Direction) is about 0.050 inches. The land width, or space between the macro-cells, is about 0.040 inches.

Figure 2A:
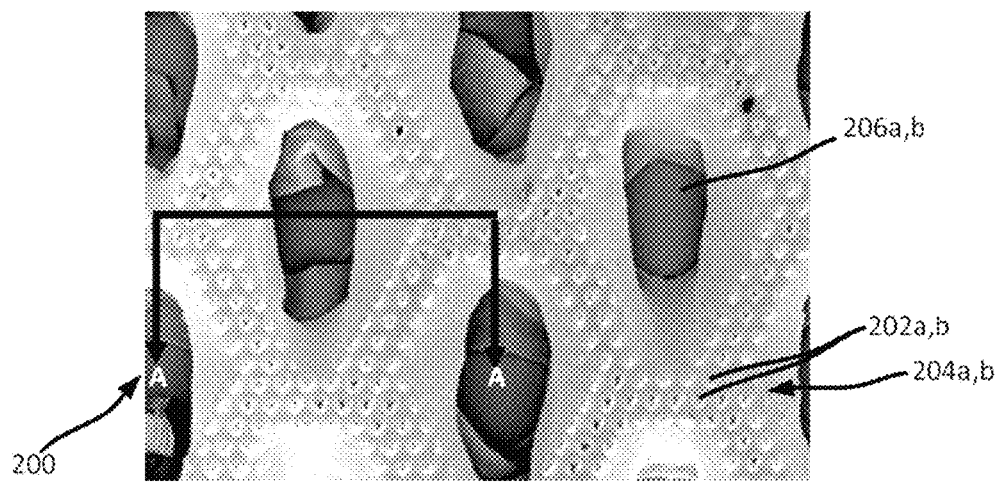
FIG. 2A depicts an example of a prior art film with micro-cells and macro-cells.
Figure 2B:
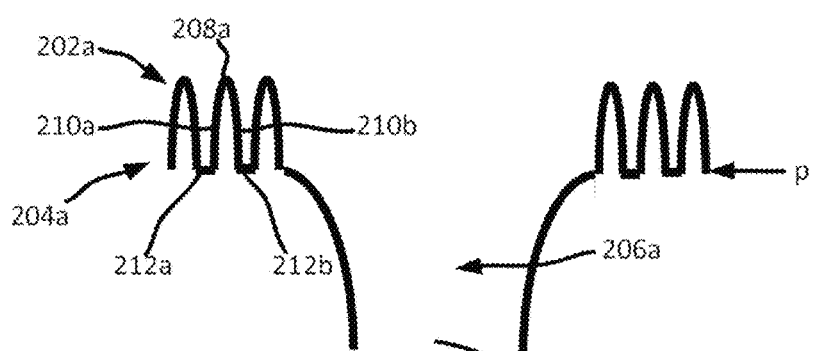
FIGS. 2B-2C depict examples of the film of FIG. 2A along lines A-A.
Figure 2C:
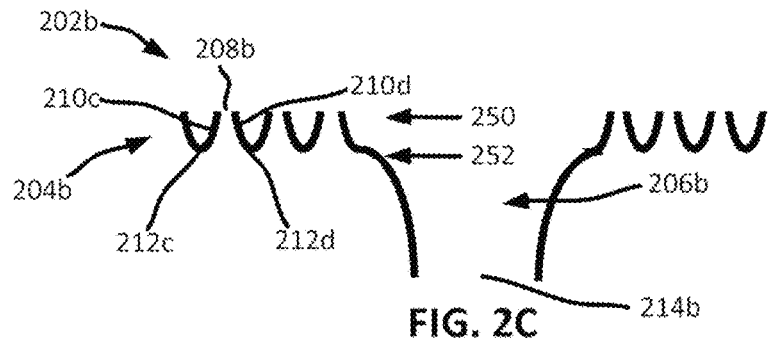

FIGS. 2A-2C depicts an example embodiment of a prior art film 200. As shown, the film 200 may include micro-cells 202a, 202b on lands 204a, 204b of the film 200. The film 200 may further include macro-apertures or holes 206a, 206b adjacent to the lands 204a, 204b. As shown in FIG. 2B, in one example, the micro-cells 202a may be closed and may extend upward from the lands 204a in a first z-direction "a" such as a direction toward skin of a user, for example, when the film 200 may be used as a topsheet in an article. For example, the micro-cells 202a may include a closed tip 208 and walls 210a, 210b. The walls 210a, 210b of a micro-cell may extend upward from a plane p of the lands 204a in the first z-direction "a" and may terminate in the closed tip 208a.

Further, as shown in FIG. 2B, the micro-cells 208 may have a particular orientation. For example, the micro-cells 208 may be oriented toward skin of a user, for example, when the film 200 may be used in the article. In such an example, the closed tips 208a may be oriented toward the skin such that the closed tips 208a may be the closest portion of the micro-cells 202a to the skin. The walls 210a, 210b may extend downward from the closed tips 208a in a second z-direction "b" such as a direction toward a core of the article. The walls 210a, 210b may terminate in a respective crest or valley portion 212a, 212b that may be oriented toward the core such that the crest or valley portions 212a, 212b may be the closest portion of the micro-cells 202a to the core. Such an example where the closed tip of the micro-cells may be closer to the skin and the walls may extend from the closed tip in a z-direction toward the core terminating in a crest or valley portion that may be closer to the core may represent a micro-cell that may be oriented toward the skin.

In an example, the macro-apertures or holes 206a may extend in the second z-direction b toward the core. For example, the macro-apertures or holes 206a may extend downward from the lands 204a such as the plane p of the lands 204 in the second z-direction "b". As shown, the micro-apertures or holes 206 may terminate in a single opening 214a. Such a single, larger opening (e.g., the opening 214a) may transmit the color of menses through to the eye of the user after the use of a sanitary napkin, for example. This may not be desireable and may be resolved by examples and embodiments described herein (e.g., as shown in FIGS. 6A-6F) whereupon a field of smaller micro-cells at the bottom the macro-cells may help to mask and deter any transmission of the menses stain to the eye of the user.

As shown in FIG. 2C, in another example, the micro-cells 202b on the lands 204b may not extend upward from a top surface of the film 200 as shown in FIG. 2B, but may include a similar orientation (e.g., toward the skin) to the micro-cells 202a in FIG. 2B. For example, the micro-cells 204b may extend between a top surface 250 and a bottom surface 252 of the film 200. In such an example, as shown in FIG. 2C, a micro-cell 202b may include an open tip 208b, walls 210c, 210d, and valley portions 212c, 212d. In an example, the open-tip 208b may not extend upward in the first z-direction "a" from the top surface 250 of the land 204b. The open tip 208b may remain generally along or near the top surface 250 of the land 204b. Further, the open tips 208b may be closer to or the closest portion of the micro-cells to the skin, for example, at the top surface 250. The walls 210c, 210d may extend downward from the open tips 208b in a second z-direction "b" such as the direction toward the core 262 of the article and may terminate in respective crest or valley portions 212c, 212d at the bottom surface 252 of the film 200. The crest or valley portion 212c, 212d may be a closest portion of the micro-cells 20b4 to the core, for example, at the bottom surface 252. Such an example where the open tip of the micro-cells may be closer to the skin (e.g., at a top surface of the film) and the walls may extend from the open tip in a z-direction toward the core terminating in crest or valley portions that may be closer to the core (e.g., at a bottom surface of the film) may further represent a micro-cell that may be oriented toward the skin.

In an example, as shown in FIG. 2C, the macro-apertures or holes 206b may extend in the second z-direction "b" toward the core. For example, the macro-apertures or holes 206b may extend downward from the lands 204b in the second z-direction. As shown, the micro-apertures or holes 206b may terminate a single opening 214b. As described herein, such a single, larger opening (e.g., the opening 214b) may transmit the color of menses through to the eye of the user after the use of a sanitary napkin, for example. This may not be desireable and may be resolved by the examples herein (e.g., as shown in FIGS. 6A-6F) whereupon a field of smaller micro-cells at the bottom the macro-cells may help to mask and deter any transmission of the menses stain to the eye of the user.

Figure 3A:
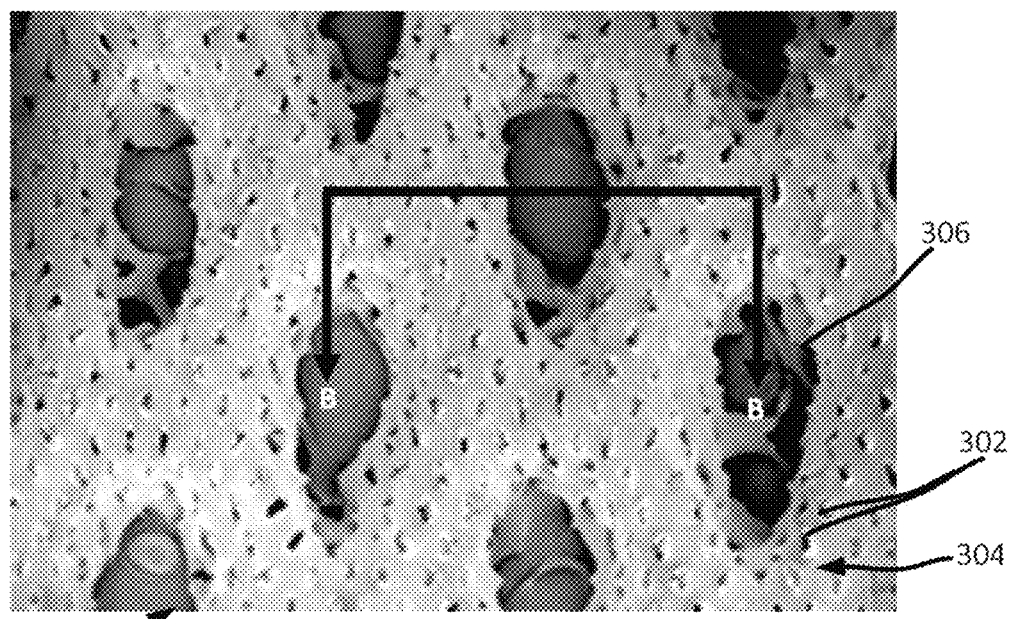
FIG. 3A depicts an example of a prior art film with micro-cells and macro-cells.
Figure 3B:
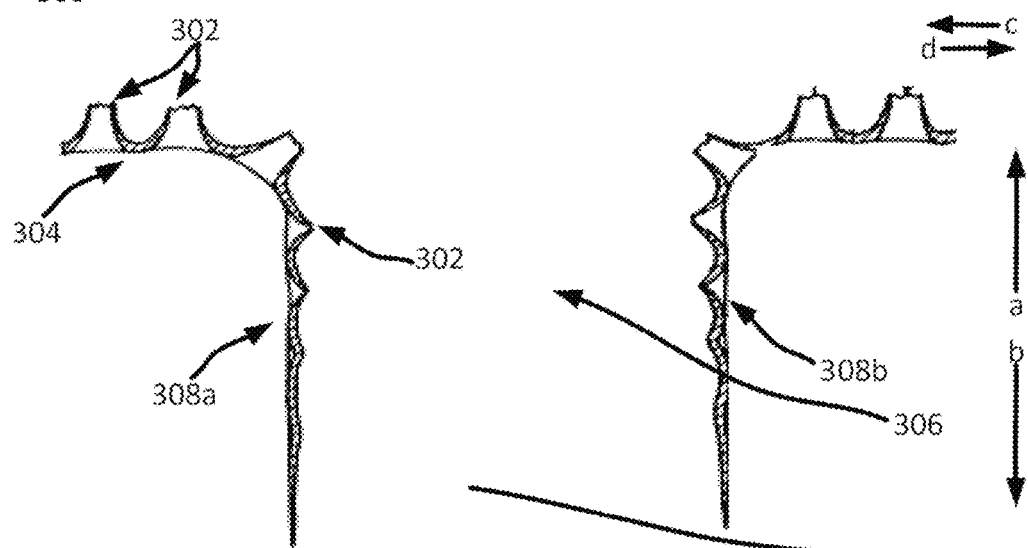
FIG. 3B depicts an example of the prior art film of FIG. 3A along lines B-B.

FIGS. 3A-3B depicts an example embodiment of a prior art film 300. As shown, the film 300 may include micro-cells 302 on lands 304 of the film 300. The film 300 may further include macro-apertures or holes 306 adjacent to the lands 304. As shown in FIG. 3B, the macro-apertures or holes 306 may include sidewalls 308a, 308b. In an example, the micro-cells 302 may continue down the sidewalls 308a, 308b of the macro-aperture or holes 306. As shown, the micro-cells 302 on the lands 304 may extend upwardly in a first z-direction "a" such as in direction toward skin of a user, for example, when the film may be used as a topsheet in an article. The micro-cells 302 on the lands 304 may be oriented in a first orientation such as toward the skin of the user. The micro-cells 302 that may continue down the sidewalls 308a, 308b may be generally oriented perpendicular to both the first and second z-directions "a", "b" such as along an x-direction "c" and "d".

The macro-aperture or hole 306 may extend in a second z-direction "b" opposite of the first z-direction "a" such as a direction toward a core that may be included in the article. The macro-apertures or holes 306 may terminate in an opening 312. Such a single, larger opening (e.g., the opening 312) may transmit the color of menses through to the eye of the user after the use of a sanitary napkin, for example. This may not be desireable and may be resolved by examples and embodiments described herein (e.g., as shown in FIGS. 6A-6F) whereupon a field of smaller micro-cells at the bottom the macro-cells may help to mask and deter any transmission of the menses stain to the eye of the user.

Figure 4A:
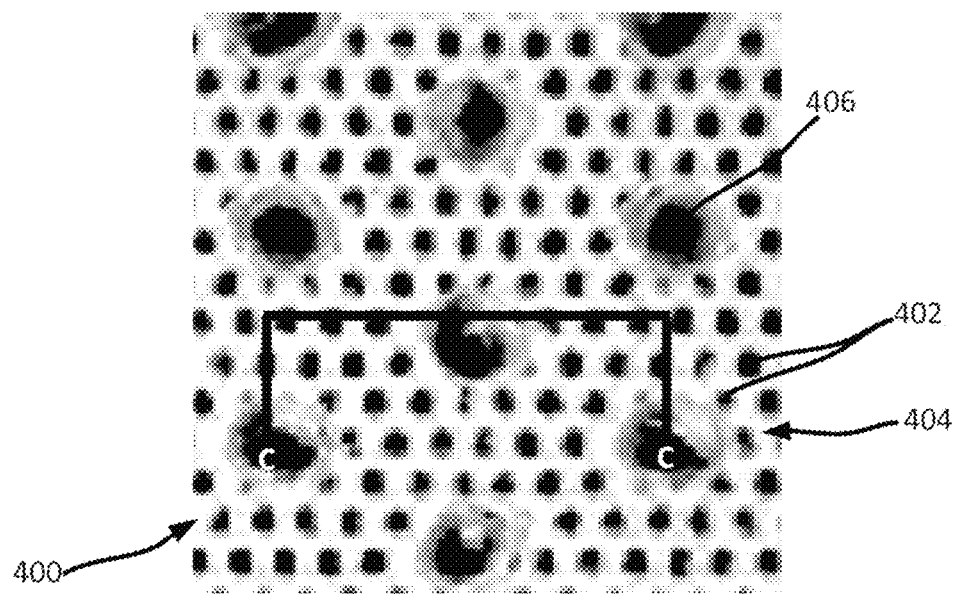
FIG. 4A depicts an example of a prior art film with micro-cells and macro-cells.
Figure 4B:
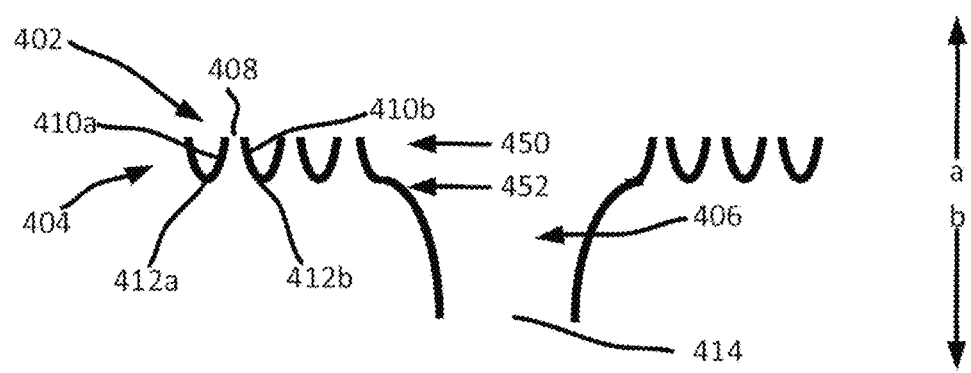
FIG. 4B depicts an example of the prior art film of FIG. 4A along lines C-C.

FIGS. 4A-4B depicts an example embodiment of a prior art film 400. As shown, the film 400 may include micro-cells 402 on lands 404 of the film 400. The film 400 may further include macro-apertures or holes 406 adjacent to the lands 404. As shown in FIG. 4B, in an example, the micro-cells 402 on the lands 404 may be oriented similar to the micro-cells 202b in FIG. 2C. For example, the micro-cells 402 may extend between a top surface 450 and a bottom surface 452 of the film 400. In such an example, a micro-cell 402 may include an open tip 408, walls 410a, 410b, and valley portions 412a, 412b. The open tip 408 may remain generally along or near the top surface 450 of the land 404. Further, the open tips 408 may be closer to or the closest portion of the micro-cells to the skin, for example, at the top surface 450. The walls 410a, 410b may extend downward from the open tips 408 in a second z-direction "b" such as the direction toward a core of the article and may terminate in respective crest or valley portions 412a, 412b at the bottom surface 452 of the film 400. The crest or valley portions 412a, 412b may be the closest portion of the micro-cells 402 to the core, for example, at the bottom surface 452. As described above, such an orientation in FIG. 4B of the micro-cells may representation micro-cells that may be oriented toward the skin.

In an example, as shown, the macro-apertures or holes 406 may extend in the second z-direction "b" toward the core. For example, the macro-apertures or holes 406 may extend downward from the lands 404 in the second z-direction "b". As shown, the macro-apertures or holes 406 may terminate an opening 414. Such a single, larger opening (e.g., the opening 414) may transmit the color of menses through to the eye of the user after the use of a sanitary napkin, for example. This may not be desireable and may be resolved by examples and embodiments described herein (e.g., as shown in FIGS. 6A-6F) whereupon a field of smaller micro-cells at the bottom the macro-cells may help to mask and deter any transmission of the menses stain to the eye of the user.

Figure 5A:
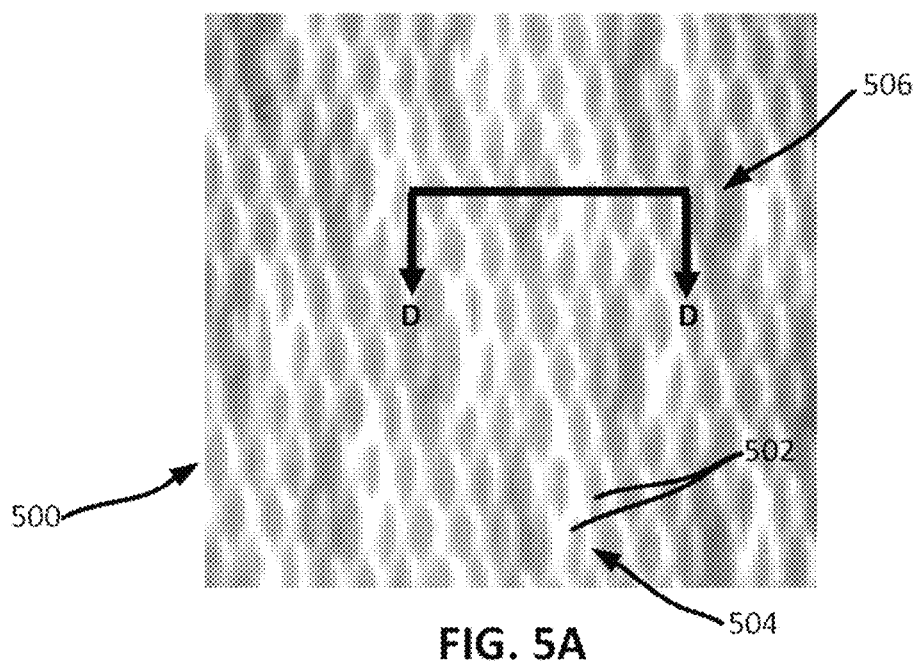
FIG. 5A depicts an example of a prior art film with micro-cells and macro-cells.
Figure 5B:
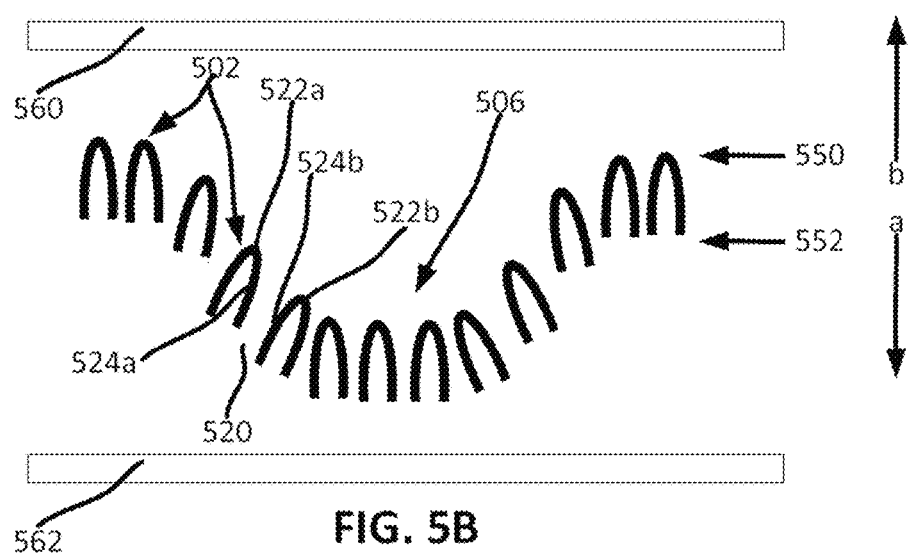
FIG. 5B depicts an example of the prior art film of FIG. 5A along lines D-D.
Figure 6A:
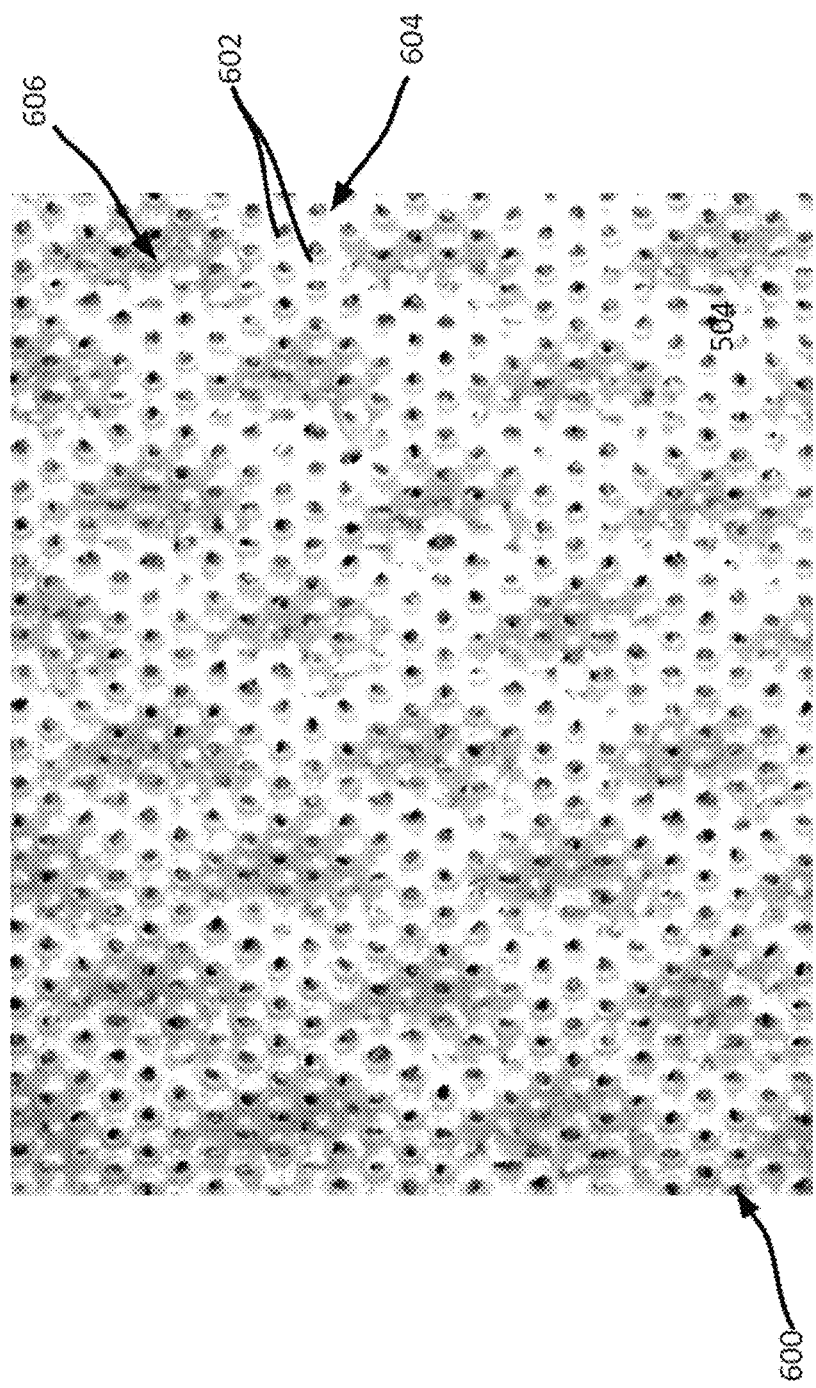
FIG. 6A depicts an example of a film that may be made with the process or method of FIGS. 1A-1C with some micro-cells pointing toward skin of a user when the film may be used in an article and other micro-cells along a macro-cell or depression pointing toward a core of the article in a macro-cell.
Figure 6B:
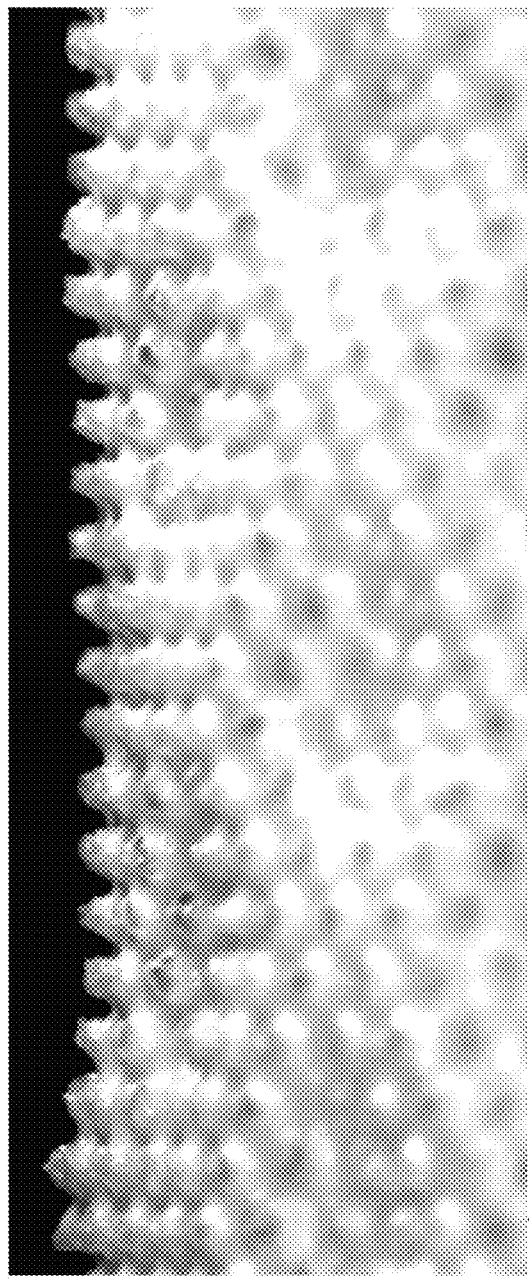
FIGS. 6B-6D depict further examples of the film of FIG. 6A.
Figure 6C:
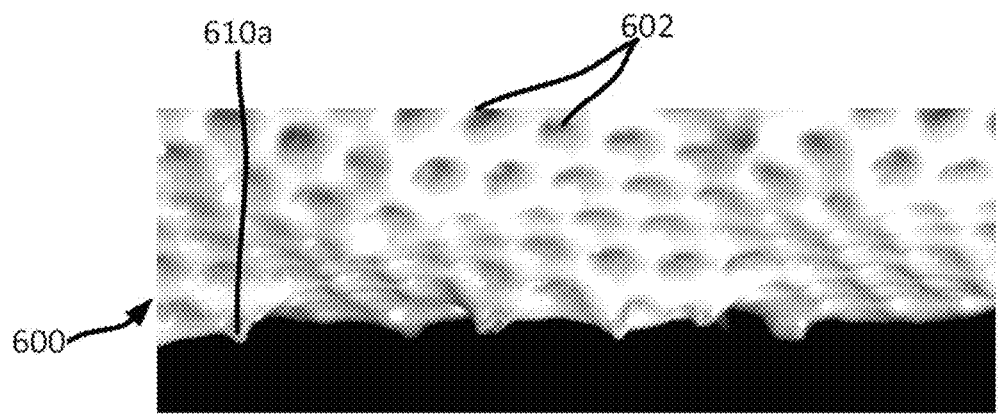
Figure 6D:
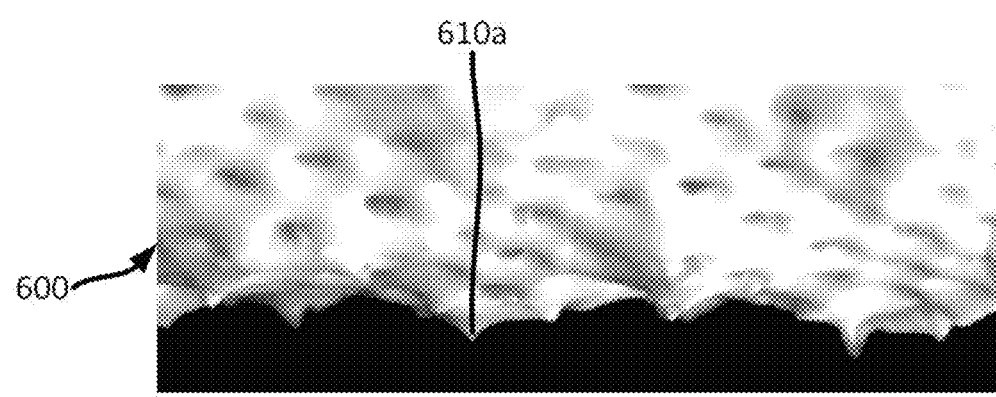
Figure 6E:
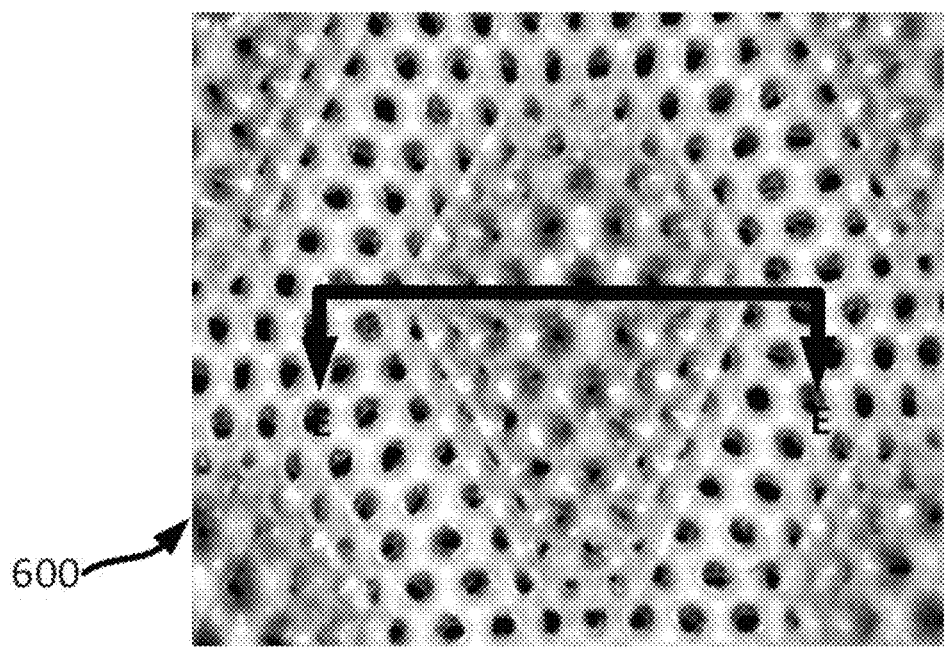
FIG. 6E depicts an example portion of part of the film of FIG. 6A.

FIGS. 5A-5B depicts an example embodiment of a prior art film 500. As shown, the film 500 may include micro-cells 502 on lands 504 of the film 500. The film 500 may further include macro-cells or depressions 506 adjacent to the lands 504. The macro-cells or depressions 506 may also include micro-cells 502 that may extend along the macro-cells depressions 506.

As shown in FIG. 5B, in an example, each of the micro-cells 502 on the lands 504 and along the macro-cells or depressions 506 may generally be oriented in the same manner. For example, the micro-cells 502 may all be oriented in a second orientation such as toward a core 562 rather than toward skin 560 of a user (e.g., a first orientation).

In such an embodiment, the micro-cells 502 may include tips 520 at a bottom surface 552 of the film 500. As shown, the tips 520 may be open-ended tips according to one example. The micro-cells 502 may further include a first and second valley 522a, 522b at the top surface 550 of the film 500 and a first and second sidewall 524a, 524b between the tips 520 and the respective first and second valleys 522a, 522b (e.g., the first sidewall 524a may be between the tip 520 and the first valley 522a and the second sidewall 524b may be between the tip 520 and the second valley 522b). As shown, the first and second sidewalls 524a, 524b may extend generally in a z-direction "b" from the tips 520 at the bottom surface 552 of the film 500 to the respective first and second valleys 522a, 522b at the top surface 550 of the film 500. Further, in an example, when the film 500 may be used in the article, the first and second sidewalls 524a, 524b may extend in the z-direction "b" toward the skin of the article. Such an example where the tips of the micro-cells may generally be near a bottom surface or a surface of the film closer to the core, the valleys may generally be near a top surface or a surface of the film closer to the skin, and the sidewalls may extend therebetween, for example, in the z-direction "b" or a direction from the tip upward toward the skin to the valleys may represent an orientation of the micro-cells such as an orientation toward the core.

FIGS. 6A-6F depict example embodiments of a film 600 having a top surface 650 and a bottom surface 652 as described herein that may include micro-cells and macro-cells where, for example, micro-cells on the lands may be oriented in one direction and at least a portion of micro-cells included in the macro-cells may be inverted (i.e., may be oriented in an opposite direction of the micro-cells on the lands). As shown, the film 600 may include micro-cells 602 on lands 604 of the film 600. In an embodiment, the micro-cells 602 on the lands 604 may have a first orientation. According to an embodiment, in the first orientation, the micro-cells 602 may be oriented toward skin 660 of a user when the film 600 may be used in an article such as a diaper.

For example, the micro-cells 602 may include tips 620 at the top surface 650 of the film 600. As shown, the tips 620 may be open-ended tips according to one example. The micro-cells 602 may further include a first and second valley 622a, 622b at the bottom surface 652 of the film 600 and a first and second sidewall 624a, 624b between the tips 620 and the respective first and second valleys 622a, 622b (e.g., the first sidewall 624a may be between the tip 620 and the first valley 622a and the second sidewall 624b may be between the tip 620 and the second valley 622b). As shown, the first and second sidewalls 624a, 624b may extend in a first z-direction "a" from the tips 620 at the top surface 650 of the film 600 to the respective first and second valleys 622a, 622b at the bottom surface 652 of the film 600. Further, in an example, when the film 600 may be used in the article, the first and second sidewalls 624a, 624b may extend in the first direction "a" toward a core 662 of the article. Such an example where the tips of the micro-cells may generally be near a top surface or a surface of the film closer to the skin, the valleys may generally be near a bottom surface or a surface of the film closer to the core, and the sidewalls may extend therebetween, for example, in the first direction "a" or a direction from the tip downward toward the core to the valleys may represent a first orientation of the micro-cells (e.g., an orientation toward the skin).

The film 600 may further include macro-cells or depressions 606 adjacent to the lands 604. As shown, the macro-cells or depressions 606 may extend, for example, downward from the lands 604 in the first direction "a". The macro-cells or depressions 606 may have first and second side portions 630a, 630b and a base portion 632. The first and second side portions 630a, 630b may extend from the lands 604 respectively toward the core 662 in the first z-direction "a" and may terminate in the base portion 632 at the bottom of the macro-cells or depressions 606.

The macro-cells or depressions 606 may include micro-cells 610a-c. The micro-cells 610a-c may extend along the macro-cells or depressions 606. As shown, in an example, the micro-cells 610a may be included along the base portion 632 of the macro-cells or depressions 606 and the micro-cells 610b, 610c may be included along the first and second side portions 630a, 630b, respectively, of the macro-cells or depressions 606.

According to an embodiment, the micro-cells 610a may have a second orientation. In the second orientation, the micro-cells 610a may be oriented toward the core 662 of a user when the film 600 may be used in an article such as a diaper. The second orientation may be an inverse of the first orientation (e.g., may include an orientation that is an inverse or opposite orientation of the first orientation).

For example, the micro-cells 610a may include tips 640 at the bottom surface 652 of the film 600. As shown, the tips 640 may be open-ended tips according to one example. The micro-cells 610a may further include a first and second valley 642a, 642b at the top surface 650 of the film 600 and a first and second sidewall 644a, 644b between the tips 640 and the respective first and second valleys 642a, 642b (e.g., the first sidewall 644a may be between the tip 640 and the first valley 642a and the second sidewall 644b may be between the tip 640 and the second valley 642b). As shown, the first and second sidewalls 644a, 644b may extend in the second z-direction "b" (e.g., a direction that may be opposite of the first direction "a") from the tips 640 at the bottom surface 652 of the film 600 to the respective first and second valleys 642a, 642b at the top surface 650 of the film 600. Further, in an example, when the film 600 may be used in the article, the first and second sidewalls 644a, 644b may extend in the second z-direction "b" toward the skin 660 of the article. Such an example where the tips of the micro-cells may generally be near a bottom surface or a surface of the film closer to the core, the valleys may generally be near a top surface or a surface of the film closer to the skin, and the sidewalls may extend therebetween, for example, in the second z-direction "b" or a direction from the tip upward toward the skin to the valleys may represent a second orientation of the micro-cells (e.g., an orientation toward the core).

Additionally, the microcells 610b, 610c may have the first orientation (e.g., similar to the micro-cells 602 on the lands 604). For example, as shown, the micro-cells 610b, 610c may include tips 670, 680 at the top surface 650 of the film 600. As shown, the tips 670, 680 may be open-ended tips according to one example. The micro-cells 610b, 610c may further include a first and second valley 672a, 672b and 682a, 682b at the bottom surface 652 of the film 600 and a first and second sidewall 674a, 674b and 684a, 684b between the tips 670, 680 and the respective first and second valleys 672a, 672b and 682a, 682b (e.g., the first sidewall 674a, 684a may be between the tip 670, 680 and the first valley 672a, 682a and the second sidewall 674b, 684b may be between the tip 670 and the second valley 672b, 682b). As shown, the first and second sidewalls 674a, 674b and 684a, 684b may extend generally in the first z-direction "a" (e.g., may extend in the first z-direction at an angle to a normal thereof) from the tips 670, 680 at the top surface 650 of the film 600 to the respective first and second valleys 672a, 672b and 682a, 682b at the bottom surface 652 of the film 600. Further, in an example, when the film 600 may be used in the article, the first and second sidewalls 674a, 674b and 684a, 684b may extend generally in the first direction "a" toward the core 662 of the article.

As described herein, the film 600 may be used as a topsheet in an article. When used as a topsheet, the top surface 650 of the film 600 may be in contact with the skin 660 during use. Further, the bottom surface 652 of the film 600 may be adjacent to or positioned near the core 662. For example, at least a portion of the bottom surface 652 of the film 600 may be in contact with the core 652. In such an embodiment, the portion of the bottom surface 652 that may be in contact with the core 652 may include the bottom surface 652 of the base portion 632 of the macro-cells or depressions 606.

Although particular shapes, sizes, and/or configurations may be described and shown for the micro-cells 602, macro-cells or depressions 606, and/or micro-cells 610a, 610b, and/or 610c in FIGS. 6A-6F, such micro-cells and/or macro-cells or depressions may include other shapes, sizes, and/or configurations. For example, the tips described herein may be open, for example, as shown in FIG. 6A-6F, closed as shown, for example, in FIG. 2B, and/or any other suitable configuration. Additionally, although the micro-cells 602, 610a, 610b, and/or 610c may generally be conical and/or the macro-cells or depressions 606 may be half a sphere, such micro-cells and/or macro-cells and/or depressions may have any other suitable shape; however, a base of the macro-cells of example prior art films may terminate with a single opening and the macro-cells of the examples described herein may be comprised of a multiplicity of micro-cells where at least about one micro-cells may be in an orientation that is inverted with respect to the orientation of micro-cells in a land adjacent to the macro-cell.

Examples

The film examples described herein can be made from a cast extrusion of a blend of 0.50% Surfactant, 3.50% Titanium Dioxide White Pigmentation particles, 30% mLLDPE, 20% HDPE and 46% Liner Grade LDPE. It may have a basis weight of 24.1 grams per square centimeter or 0.001 inch base thickness. The base sheet 18 prior to entering the process of FIG. 1 may be comprised of a 60 mesh pattern of micro-cells. The base sheet 18 may include pattern loft of about 0.010 inches. After creating the macro-cells of this invention the loft of the finished material in this example about may be 0.026 inches. In other patterns of micro and macro cell embodiments, the base sheet of micro-cells may have a loft from about 0.006 to about 0.015 inches, and the material after the macro-cells may be employed may have a loft from about 0.0015 to about 0.045 inches, depending the various combinations that can be utilized. The base sheet of 60 mesh may be made both by hydroforming and vacuum forming; however, if made by vacuum forming the base material should put in-line into the process of the embodiments described herein. If left to age from about 12-24 hours it may become too crystalline for the micro-cells at the base of the macro-cell to invert into an orientation toward the core.

Although systems, methods, processes, and/or embodiments may be described herein with respect to various materials, techniques, equipment, such systems, methods, processes, and/or embodiments may be applicable to other applications and environments and may include additional materials, equipment and manufacturing techniques, methods, and/or processes in different orders than those disclosed herein.

What is claimed:

1. A film having a top surface and a bottom surface, the film comprising:
    a plurality of lands,
        wherein the plurality of lands establishes a first area of the film,
        wherein the plurality of lands encompasses a plurality of first, apertured micro-cells,
        wherein each of the plurality of first, apertured micro-cells comprises a first open tip at the top surface of the film and a first and a second valley at the bottom surface of the film flanking either side of the first open tip,
        wherein a first sidewall extends from the first open tip to the first valley and a second sidewall extends from the first open tip to the second valley, and
        wherein the first and second sidewalls extend downward from the first open tip at the top surface of the film to the respective first and second valleys at the bottom surface of the film in the first z-direction;

a plurality of macro-depressions disposed adjacent to the plurality of lands, wherein the plurality of macro-depressions establishes a second area of the film, wherein the second area extends downward from the first area in a first z-direction from the top surface to the bottom surface, wherein the plurality of macro-depressions encompasses a plurality of second, apertured micro-cells, wherein the plurality of second, apertured micro-cells comprises a second open tip at the bottom surface of the film and a third and a fourth valley at the top surface of the film flanking either side of the second open tip, wherein a third sidewall extends from the second open tip to the third valley and a fourth sidewall extends from the second open tip to the fourth valley, and wherein each of the plurality of macro-depressions comprises a first side portion, a second side portion, and a base portion, the first and second side portions extending downward in the first z-direction from the lands, terminating in the base portion; and a plurality of third, apertured micro-cells extending along the first and side portions of the macro-depressions.

2. The film of claim 1, wherein the third and fourth sidewalls extend upward from the second open tip at the bottom surface of the film to the respective third and fourth valleys at the top surface of the film in a second z-direction that is opposite to the first z-direction, from the bottom surface to the top surface.

3. The film of claim 1, wherein the plurality of second, apertured micro-cells extends along at least a portion of the base portion.

4. The film of claim 1, wherein each of the plurality of third, apertured micro-cells comprises a third open tip at the top surface of the film, a fifth and a sixth valley at the bottom surface of the film flanking either side of the third open tip, a fifth sidewall extending from the third open tip at the top surface of the film to the fifth valley at the bottom surface of the film, and a sixth sidewall extending from the third open tip to the sixth valley at the bottom surface of the film.

5. The film of claim 4, wherein the fifth and sixth sidewalls extend downward from the third open tip at the top surface of the film to the respective fifth and sixth valleys at the bottom surface of the film in the first z-direction.

6. The film of claim 1, wherein the plurality of macro-depressions are arranged in a pattern of cells, and the cells are least one of hexagonal, circular, oval, elliptical, or polygonal.

7. The film of claim 1, wherein the plurality of macro-depressions are arranged in a pattern of cells, wherein each cell has a shape of half a sphere.

8. The film of claim 1, wherein the plurality of first, apertured micro-cells and the plurality of second, apertured micro-cells comprise mesh counts greater than 35 and wherein the plurality of macro-depressions comprise a mesh count less than 35.

9. The film of claim 1, wherein the plurality of first, apertured micro-cells and the plurality of second, apertured micro-cells comprise a mesh count of 60.

10. The film of claim 1, wherein the plurality of first, apertured micro-cells and the plurality of second, apertured micro-cells are conical.

11. The film of claim 1, wherein the film has a loft from about 0.0015 to about 0.045 inches.

* * * * *